United States Patent [19]

Marquis et al.

[11] 4,041,078

[45] Aug. 9, 1977

[54] METHOD OF PREPARING POLYAMINOPOLYPHENYLMETHANES

[75] Inventors: Edward T. Marquis; Lewis W. Watts, Jr., both of Austin, Tex.

[73] Assignee: Texaco Development Corporation, New York, N.Y.

[21] Appl. No.: 728,085

[22] Filed: Sept. 30, 1976

[51] Int. Cl.$^2$ .............................................. C07C 85/24
[52] U.S. Cl. ...................... 260/570 D; 260/453 AM; 252/441
[58] Field of Search .................... 260/570 D; 252/441

[56] References Cited

U.S. PATENT DOCUMENTS 3,362,979  1/1968  Bentley ............................ 260/570 X

*Primary Examiner*—Robert V. Hines
*Attorney, Agent, or Firm*—Carl G. Ries; Thomas H. Whaley; James L. Bailey

[57] ABSTRACT

Covers a method of preparing diaminodiphenylmethanes and higher homologues thereof which comprises the step of condensing aniline and formaldehyde in the presence of a fluorinated graphite catalyst.

3 Claims, No Drawings

METHOD OF PREPARING POLYAMINOPOLYPHENYLMETHANES

BACKGROUND OF THE INVENTION

1. Field of the Invention

This invention relates to the field of polyamines.

2. Description of the Prior Art

The process of producing aromatic polyamines by the reaction of aniline and formaldehyde is well known and described for example in U.S. Pat. Nos. 2,683,730; 3,277,173; 3,344,162; and 3,362,979. By phosgenating these amines the corresponding isocyanates are obtained. The polyamines produced by the condensation of aniline and formaldehyde usually consist of a mixture of poly-(methylenephenylamines) of functionality greater than two and the 2,2', 2,4' and 4,4' isomers of diaminodiphenylmethane. By reaction with phosgene a corresponding mixture of polyisocyanates and diisocyanates is prepared which is useful in producing, for example, polyurethane foam.

One mode of reacting aniline with formaldehyde is to effect this reaction in the presence of a strong mineral acid, such as hydrochloric acid. Here a reaction occurs between the corresponding aniline hydrochloride and formaldehyde to provide a reaction mixture which, upon neutralization with a base, may be treated to recover the polyphenylamines. This process has left much to be desired. For example, it is necessary to utilize large quantities of both a mineral acid and a base which adversely affect the economics of the process and also the ease of conducting the reaction. In addition, the use of large quantities of mineral acids and bases presents a severe corrosion problem. Also, the inorganic salt formed poses environmental difficulties with respect to disposal and/or recovery.

As an improvement to the conventional mineral acid catalyzed aniline-formaldehyde condensation use of a solid acidic siliceous catalyst has been proposed (see U.S. Pat. No. 3,362,979). This is economically favorable over the conventional hydrochloric acid catalyzed process since use of large quantities of corrosive acid and caustic are avoided. However, even this process has some drawbacks, particularly, in that the rate of reaction is not as rapid as desired and rearrangement of product amines at conventional conditions is not considered sufficiently complete.

SUMMARY OF THE INVENTION

The invention relates to a process for making aromatic polyamines by the reaction of aniline and formaldehyde in the presence of a fluorinated graphite catalyst.

DESCRIPTION OF THE PREFERRED EMBODIMENTS

A method of preparing diaminodiphenylmethane and higher homologues thereof has now been discovered. The invention comprises the step of condensing aniline and formaldehyde in the presence of a fluorinated graphite catalyst. A mixture of products is produced which includes the diaminodiphenylmethane isomers comprising the 2,2', 2,4', and 4,4' diamine isomers and higher homologues thereof or polymethylene polyphenylamines. The latter are higher molecular weight condensation polymers of the formaldehyde and the aniline and are considered homologues of the simple diaminodiphenylmethane isomers.

Depending upon reaction conditions, amount of catalyst employed, proportions of the reactants, and other variables the proportions of diamines, and higher polyamines present in the final reaction mixture may be widely varied. However, usually the reaction mixture contains 20–80 percent by weight of diamine with the remainder being higher polyamines thereof. More often the percentage of diamines in the mixture is 30–70 percent and most often ranges from about 35 to about 55 weight percent. Correspondingly the polymeric products higher than the dimer products usually in the preferred embodiment range from the 30 to 70 percent by weight, and most often range from about 45 to about 65 percent by weight. With respect to product distribution of the dimer usually 1–10 percent by weight of total dimer is the 2,2' isomer, with the remainder being 2,4' and 4,4' isomers. Most often the content of dimer is 1–5 percent 2,2' isomer with the remainder, or 95–99 percent being 2,4' and 4,4' isomers, based on total dimer content. Generally the higher molecular weight polymethylene polyphenylpolyamines have an average functionality of from about 2.1 to about 3.0, more often 2.2–2.7.

The fluorinated graphite catalyst is a known material which is prepared by reacting graphite with fluorine, halogen fluoride, or higher fluorine-containing compounds. Typical means of producing fluorinated graphites are described, for example, in U.S. Pat. No. 3,397,087 and British Pat. No. 1,049,582. A typical fluorinated graphite exists as a light gray powder of a composition having the formula $(CF_x)_n$ where X is between 0.90 and 1.00. A typical fluorinated graphite will analyze as 40 weight percent carbon and 60 weight percent fluorine with less than 0.3 weight percent free fluoride.

One commercially available fluorinated graphite has the following physical properties.

| | |
|---|---|
| Melting Point | Does not melt |
| Particle Size | 50% 2 – 9.2 microns |
| | 35% 9.2 – 20 microns |
| | 15% 20 – 50 microns |
| Density | 169.8 lb/cu ft (2.72 g/cu cm) |
| Bulk Specific Gravity | 0.3 – 0.4 |
| Heat of Combustion | 3,487 ± 20 cal/g |
| Autoignition Temperature | |
| Air | 1137 ± 40° F (613.9 ± 4.4° C) |
| 100% Oxygen | 1108 ± 40° F (597.8 ± 4.4° C) |

The amount of fluorinated graphite catalyst used here may be varied according to the choice of the experimenter. Usually, however, 0.5 – 3.0 percent by weight of catalyst based on weight on aniline is employed. More often, the amount of catalyst utilized is 1 – 2 percent by weight based on aniline weight.

In order to prepare the methylene-bridged polyphenyl polyamines (term includes both diaminodiphenylmethane isomers and higher homologues thereof or higher polymers) the following process conditions are preferred.

The molar ratio of aniline to formaldehyde may be varied within comparatively wide limits. Thus, for example, from about 1 to about 10 mols of aniline may be employed per mol of formaldehyde. In general, at the lower aniline: HCHO ratios, such as ratios of from about 1:1 to about 2.5:1, the higher polymers will be formed preferentially and the yield of higher polymers is in excess of the yield of dimer. However, as progressively larger amounts of aniline are used, the yield of dimer is progressively increased at the expense of polymer yield. Thus, with aniline to formaldehyde ratios of from about 3:1 to about 10:1 or more, the reaction product will be composed primarily of dimer. As indicated above, the dimer will be formed as a mixture of the 2,4'- and 4,4'-diamine isomers.

Formaldehyde may be employed in any of its commercially available forms. Thus, formalin, paraformaldehyde, "stabilized" methanol solutions of formaldehyde, etc., may be employed.

The reaction may be conducted in the presence or absence of a solvent. When a solvent is to be employed, it may be any of the conventionally known hydrocarbon solvents or chlorinated hydrocarbons, such as aromatic or aliphatic solvents boiling within the range from about 100° to about 200° C. The solvent should be employed in an amount sufficient to provide a single phase solution of the amine compound.

The reaction conditions to be employed may suitably include a reaction temperature within the range of about 100° to about 300° C, and more preferably within the range of about 150° to about 250° C.

Pressure is not particularly critical with respect to the process. However, the pressure should be sufficient to provide a liquid phase reaction conditions. Thus, pressures ranging from atmospheric up to 1000 psig may be employed.

The reaction proceeds smoothly under the above-described conditions, and is normally substantially complete upon addition of the formaldehyde. However, because of the exothermic nature of the reaction, it is normally preferable to add the formaldehyde at a rate such that the desired reaction temperature can be maintained. It is normally possible to bring the reaction to completion within from about 5 minutes to about 8 hours in conventional equipment. More often the reaction is complete in $\frac{1}{2}$ - 4 hours.

The polyaminopolyphenylmethanes of the present invention are recovered from the reaction mixture by any desired means. They are conveniently recovered by filtering the catalyst and removing water and excess aniline under reduced pressure. The bottoms from these operations will consist of diamine and polyamine in proportions depending on the ratio of aniline to formaldehyde, as indicated above. If it is desired to separate the diamine from the polyamine, this is easily accomplished by simple distillation whereby the diamine is flashed from the non-volatile polyamine residue. The overhead product may be removed, for example, at from about 170° to about 200° C at about 0.5 to about 0.025 mm. Hg pressure and will consist essentially of diaminodiphenylmethane.

The dimer and higher products of the present invention are useful for a variety of purposes. For example, they may be utilized as raw materials for the production of the corresponding polyisocyanates, or used as such as epoxy curing agents.

The advantages in using a fluorinated graphite catalyst in the process of the invention are many and varied. In the first place a completely rearranged product is achieved in a desirable manner. In addition, many commonly used catalysts such as hydrochloric acid are highly corrosive whereby there is no indication here that the catalysts used here are corrosive in any manner. Again, it has been found that the fluorinated graphites are considerably more active than other known catalysts such as silica-alumina, which latter catalyst does, however, avoid the discussed problems of corrosion. Again, only small amounts of catalyst need be employed and the catalyst is readily removed from the reaction mixture by filtration. Surprisingly, relatively complete rearrangement of product amine occurs at conditions which, with silica-alumina catalyst, do not afford a suitable product.

The following examples illustrate the process of the invention. It is understood, of course, that these examples are merely illustrative, and that the invention is not to be limited thereto.

EXAMPLE 1

Aniline (186.0 g, 2.0 moles), formalin (30.0 g of formaldehyde or 1.0 mole formaldehyde) and 1.9 g of fluorinated graphite (1 percent by weight basis aniline charged, from Ventron, Alfa Inorganics, $[CF_x]_n$ where $x = 0.93$) were all added to a 1-l. stirred stainless steel autoclave and the clave flushed with $N_2$ before heating to 200° C, where it was held for 1 hour at autogenous pressure (with stirring). The crude reactor effluent was stripped of water, filtered, and the aniline stripped, affording a product amine with 9.60 meq/g total titratable amine content, molecular weight of 286 Mn, GLC of 43.8% MDA content and a 63.2% 4,4'-isomer content in the MDA or dimer portion of the polyamine. The NMR spectrum indicated the product amine contained no unrearranged N-benzyl secondary amines and only 5.9% N-methyl secondary amines.

EXAMPLE 2

Aniline (232.5 g, 2.5 moles), formalin (30 g formaldehyde, 1.0 mole formaldehyde), and fluorinated graphite (2.3 g, 1.0 percent by weight basis aniline charged, Ventron, Alfa Inorganics, $[CF_x]_n$ where $x = 0.93$) were charged to a 1-l. stirred autoclave. After flushing with $N_2$, the mixture was heated to 200° C and held there at 200° C for 2 hours at autogenous pressure. The crude reactor effluent was stripped of water, filtered and stripped of aniline. The product amine had 9.63 meq/g of titratable amine content and contained only 0.5 ppm. Fe indicating the non-corrosiveness of the catalyst toward stainless steel. Further, the NMR spectrum indicated no secondary N-benzyl amines and only 4.9% N-methyl secondary amines. The GLC indicated 51.6% MDA content of which 66.4% is the 4,4'-isomer.

EXAMPLE 3

Aniline (372 g, 4.0 moles), formalin (30 g formaldehyde, 1.0 mole formaldehyde) and fluorinated graphite (3.7 g, 1.0 percent by weight basis aniline charged, Ventron, Alfa Inorganics, $]CF_x]_n$ where $x = 0.93$) were charged to a 1-l. stirred autoclave. After flushing with $N_2$, the mixture was heated to 200° C and held there for 2 hours, at autogenous pressure. Work-up similar to that in Example 2 afforded product amine with 9.80 meq/g total titratable amine content. The NMR spectrum indicated a very high quality amine with no N-benzyl secondary amine content and only 1.4% N-methyl secondary amine content. The GLC indicated 64.6 percent by weight MDA of which the 4,4'-MDA was 65.9 percent. The GPC indicated a product distribution consisting of 60% dimer (MDA isomers) 24 trimer, and 17% heavier homologues.

EXAMPLE 4

Aniline (465 g, 5.0 moles), formalin (30 g formaldehyde, 1.0 mole formaldehyde) and fluorinated graphite (4.7 g, 1.0 percent by weight basic aniline charged, Ventron, Alfa Inorganics, $[CF_x]_n$ where $x = 0.93$) were charged to a 1-l. stirred autoclave. After flushing with N₂, the mixture was heated to 250° C and held there for 2 hours. Work-up similar to that described in Example 2 afforded a product amine with 9.40 meq/g total titratable amine content, and 2.8 ppm. Fe, again emphasizing the apparent non-corrosiveness of this catalyst. The NMR spectrum indicated the absence of N-benzyl secondary amine and the presence of only 1.9% N-methyl secondary amine. The GLC of the product amine indicated an MDA content of 63.8 percent (wt. %) with 51.8 percent of the MDA being the 4,4'-isomer.

We claim:
1. A method of preparing diaminodiphenylmethane and higher homologues thereof which comprises the step of condensing aniline and formaldehyde in the presence of a fluorinated graphite catalyst.
2. The method of claim 1 wherein said catalyst is present in an amount ranging from about 0.5 to about 3.0 percent by weight based on the weight of aniline present.
3. The method of claim 2 wherein said catalyst is present in an amount of 1-2 percent by weight.

* * * * *